(12) United States Patent
Keller

(10) Patent No.: US 11,877,864 B2
(45) Date of Patent: Jan. 23, 2024

(54) VOLTAGE NULLING PRESSURE SENSOR PREAMP

(71) Applicant: Silicon Microstructures, Inc., Milpitas, CA (US)

(72) Inventor: Craig A. Keller, Boulder, CO (US)

(73) Assignee: MEASUREMENT SPECIALTIES, INC., Hampton, VA (US)

( * ) Notice: Subject to any disclaimer, the term of this patent is extended or adjusted under 35 U.S.C. 154(b) by 1116 days.

(21) Appl. No.: 16/568,150

(22) Filed: Sep. 11, 2019

(65) Prior Publication Data

US 2020/0375540 A1 Dec. 3, 2020

Related U.S. Application Data

(60) Provisional application No. 62/854,255, filed on May 29, 2019.

(51) Int. Cl.
| | | |
|---|---|---|
| *A61B 5/00* | (2006.01) | |
| *G01L 1/22* | (2006.01) | |
| *G01L 1/18* | (2006.01) | |
| *G01L 9/00* | (2006.01) | |
| *G01K 7/16* | (2006.01) | |

(52) U.S. Cl.
CPC .............. *A61B 5/6847* (2013.01); *G01K 7/16* (2013.01); *G01L 1/18* (2013.01); *G01L 1/2262* (2013.01); *G01L 1/2281* (2013.01); *G01L 9/0052* (2013.01); *A61B 2562/0247* (2013.01)

(58) Field of Classification Search
CPC .......... A61B 5/6847; A61B 2562/0247; G01L 1/2262; G01L 1/2281; G01L 1/18; G01L 9/0052; G01L 1/225; G01K 7/16
See application file for complete search history.

(56) References Cited

U.S. PATENT DOCUMENTS

| | | | |
|---|---|---|---|
| 4,190,804 A | * | 2/1980 | Pyne ........................ G01L 9/065 327/513 |
| 4,192,005 A | | 3/1980 | Kurtz |

(Continued)

FOREIGN PATENT DOCUMENTS

| | | |
|---|---|---|
| FR | 2671651 A1 | 7/1992 |
| GB | 1591620 A | 6/1981 |
| JP | 2013156171 A | 8/2013 |

OTHER PUBLICATIONS

Samaun, et al., "An IC Piezoresistive Pressure Sensor for Biomedical Instrumentation", IEEE Transactions on Biomedical Engineering, vol. 20, No. 2, Apr. 1973, 19 pages.

(Continued)

*Primary Examiner* — Farhana A Hoque
*Assistant Examiner* — Joseph O Nyamogo

(57) ABSTRACT

Pressure sensors that can be reliability operated with the maximum current flowing through the device restricted to 10 uA or below, or below 50 uA in a single-fault condition. This can provide at least a reduced need for the final medical device architect to consider potential risks from excessive current to the patient, simplifying the design and manufacturability of the medical device. An additional benefit is that the sensors are generally more accurate at lower current flow, as self-heating of the resistors and parasitic leakages are reduced, if the signal-to-noise problem is resolved.

20 Claims, 3 Drawing Sheets

(56) References Cited

U.S. PATENT DOCUMENTS

| | | | |
|---|---|---|---|
| 4,329,641 A * | 5/1982 | Ikeda | G01R 15/09 |
| | | | 324/99 D |
| 4,659,235 A | 4/1987 | Gilmore, Jr. et al. | |
| 4,777,952 A * | 10/1988 | Pavel | A61N 1/38 |
| | | | 607/45 |
| 5,187,985 A * | 2/1993 | Nelson | G01L 1/2281 |
| | | | 338/3 |
| 5,511,301 A | 4/1996 | McGuire | |
| 5,686,826 A | 11/1997 | Kurtz et al. | |
| 5,902,248 A | 5/1999 | Millar et al. | |
| 6,198,296 B1 * | 3/2001 | Ivanov | G01D 3/021 |
| | | | 307/131 |
| 6,285,958 B1 | 9/2001 | Wolf et al. | |
| 6,394,986 B1 | 5/2002 | Millar | |
| 6,585,660 B2 | 7/2003 | Dorando et al. | |
| 7,097,620 B2 | 8/2006 | Corl et al. | |
| 7,191,072 B2 | 3/2007 | Champion et al. | |
| 9,429,479 B2 | 8/2016 | Millar et al. | |
| 2010/0076606 A1 * | 3/2010 | Gatley | F24F 11/77 |
| | | | 700/282 |
| 2011/0098584 A1 | 4/2011 | Plouf et al. | |
| 2012/0283583 A1 * | 11/2012 | Batkin | A61B 5/025 |
| | | | 600/499 |
| 2015/0249434 A1 * | 9/2015 | Ogawa | H03F 3/45932 |
| | | | 330/296 |
| 2018/0013283 A1 * | 1/2018 | Liu | H02H 9/02 |
| 2019/0158077 A1 * | 5/2019 | Tillotson | G01D 3/036 |

OTHER PUBLICATIONS

Extended European Search Report, European Application No. 20176454.5-1001, European Filing Date, Oct. 10, 2020.

* cited by examiner

VOLTAGE NULLING PRESSURE SENSOR PREAMP

CROSS REFERENCE TO RELATED APPLICATIONS

This application claims the benefit of provisional patent application 62/854,255, filed May 29, 2019, which is incorporated by reference.

BACKGROUND

Since their introduction in the 1980s, the role of pressure sensors used inside the body during medical procedures has grown steeply, with no end in sight. This demand arises partly from the rise in minimally invasive surgery, in which surgeons cannot see the treatment site directly and rely instead on sensor feedback to guide their hands, and also from the development of transcatheter and endoscopic therapies in an ever-increasing number of procedures. The success of these sensors is advanced by the ability to calibrate them for accurate pressure readings and to operate them in a manner that is safe for both the patient and the medical staff. Finally, these devices should be amenable to high-volume manufacture. These requirements can come in conflict, absent a device and procedure designed to accommodate all of them.

More specifically, one type of sensor that is in increasing demand is the solid-state electronic piezoresistive pressure sensor, based on the piezoresistive effect manifested in semiconductors (or metal strain gauges). The piezoresistive effect is a change in the electrical resistivity of a semiconductor when mechanical strain is applied. Changes in pressure against the membrane change its shape and mechanical strain, and this change in turn generates a detectable change in the electrical resistance of one or more resistors on the membrane. Typically the change in resistance is detected by passing a current through the resistors and detecting a voltage change or by applying a voltage across the resistors and detecting a current change. However, safety regulations restrict the amount of current that the patient can be exposed to. Currents exceeding these values risk inducing cardiac arrhythmia, among other problems. For example, an American National Standards Institute specification by the Association for the Advancement of Medical Instrumentation, ANSI/AAMI ES60601-1:2005 (r2012). Within this standard, Table 3 describes currents limits that are considered safe for patients. The standard limits the patient auxiliary current to less than 10 µA during normal operation and 50 µA during single-fault operation. In typical commercially-available solid-state pressure transducers, this current is far below optimal currents based on signal-to-noise considerations and self-heating limitations. This places the burden of containing the so-called "risk current" on the designer of the final medical device, who must carefully shield the sensor and cabling from making any direct contact to the patient.

Thus, what is needed are sensors that can be reliability operated with the maximum current flowing through the device restricted to 10 uA or below, or below 50 uA in a single-fault condition.

SUMMARY

Accordingly, embodiments of the present invention can provide sensors that can be reliability operated with the maximum current flowing through the device restricted to 10 uA or below, or below 50 uA in a single-fault condition. Thus, there is at least a reduced need for the final medical device architect to consider potential risks from excessive current to the patient, simplifying the design and manufacturability of the medical device. An additional benefit is that the sensors are generally more accurate at lower current flow, as self-heating of the resistors and parasitic leakages are reduced, if the signal-to-noise problem is resolved.

FIG. 1A illustrates a pressure sensor that can be improved by an embodiment of the present invention. The resistance of this type of pressure transducer changes with changes in environmental pressure. These transducers are typically used in a Wheatstone bridge configuration. An example of this configuration is shown in FIG. 1B with element B1 having a negative coefficient of resistance with pressure and with element B2 having a positive coefficient of resistance with pressure. In one typical Wheatstone bridge configuration, a current is passed through the bridge from node A to node D (this is the excitation current) and a pressure dependent voltage is read across nodes B and C.

In addition to being sensitive to pressure, the resistances of the pressure-sensitive elements B1 and B2 are also typically sensitive to temperature. In the configuration shown in FIGS. 1A and 1B, a temperature change causes a common mode change in the resistance of elements B1 and B2 while a change in the ambient pressure around the sensor causes the two elements to change in opposite directions, generating a differential voltage between nodes B and C. It is common practice to measure both common mode and differential mode changes in the resistance of the pressure sensitive elements. This allows, after appropriate calibration, the pressure and temperature of the pressure sensitive elements to be determined. In particular, performing both measurements allows the calibration of the pressure signal to compensate for temperature-dependent effects, increasing the accuracy of the pressure measurement at any temperature.

The excitation current is typically chosen to be large enough to produce an easily read voltage and small enough to avoid significant self-heating of the sensing elements in the bridge. However, in invasive medical devices, the additional constraint of patient safety requires additional elements (resistors) to restrict the current passing through the sensor. This in turn means that the pressure-induced voltage change in the bridge (the signal measured across nodes B and C) becomes extremely small. At the same time, the resistors used to limit the current introduce voltage and/or current fluctuations (typically Johnson noise). These two effects together can create a poor signal-to-noise ratio.

The circuit disclosed here improves the ratio of the signal to noise (SNR) by allowing relatively small resistors to be used as current limiting elements and by minimizing the impact of the voltage-limiting elements (for example, diodes) on the signal from the bridge. The voltage-limiting elements are active during a fault condition to reduce the current that the patient could be exposed to. During normal operation the output voltage of the bridge and thus the voltage across the voltage-limiting elements can be held close to zero by a feedback circuit configured to feed a differential current back into the bridge. The differential voltage required to generating the nulling current can be proportional to the output voltage of the bridge without the nulling current. This differential voltage can be the pre-calibration pressure output of the circuit.

Various embodiments of the present invention can incorporate one or more of these and the other features described herein. A better understanding of the nature and advantages of the present invention can be gained by reference to the following detailed description and the accompanying drawings.

DESCRIPTION OF ILLUSTRATIVE EMBODIMENTS

Figure 1A:
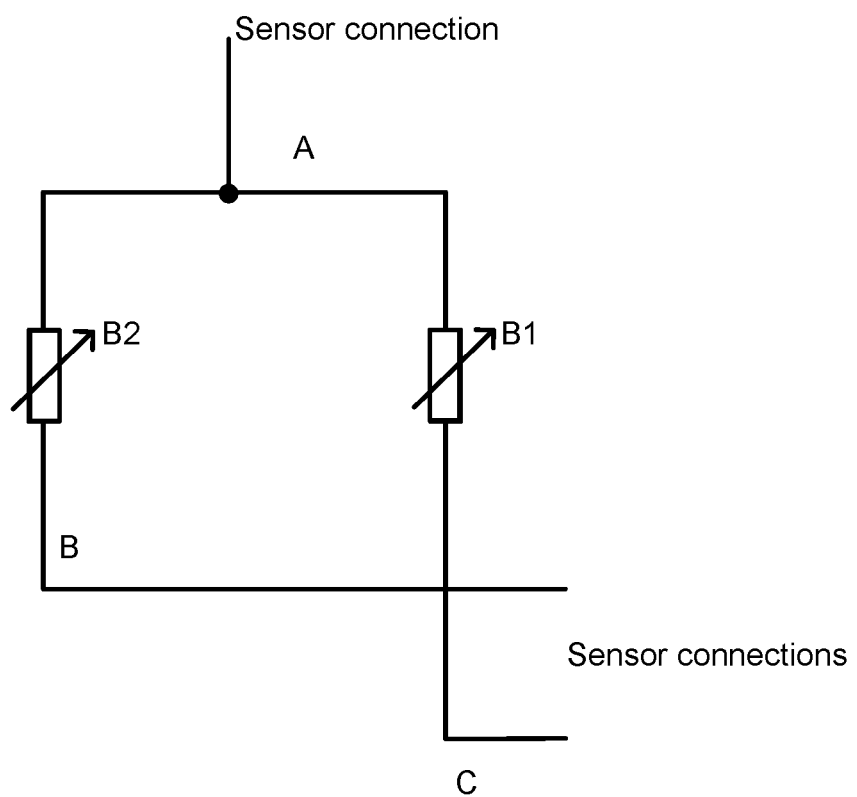
FIGS. 1A and 1B illustrate pressure sensing circuits that can be improved by the incorporation of an embodiment of the present invention.
Figure 1B:
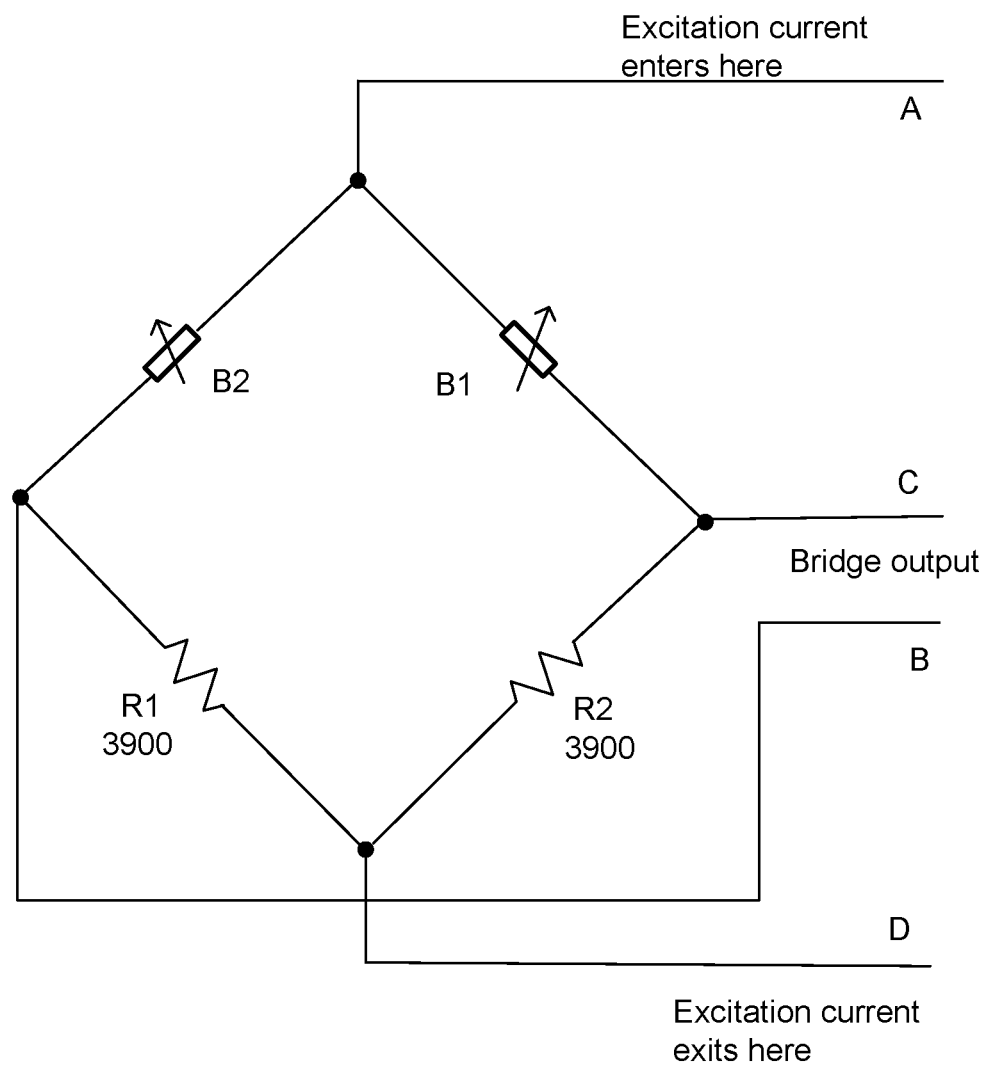
Figure 2:
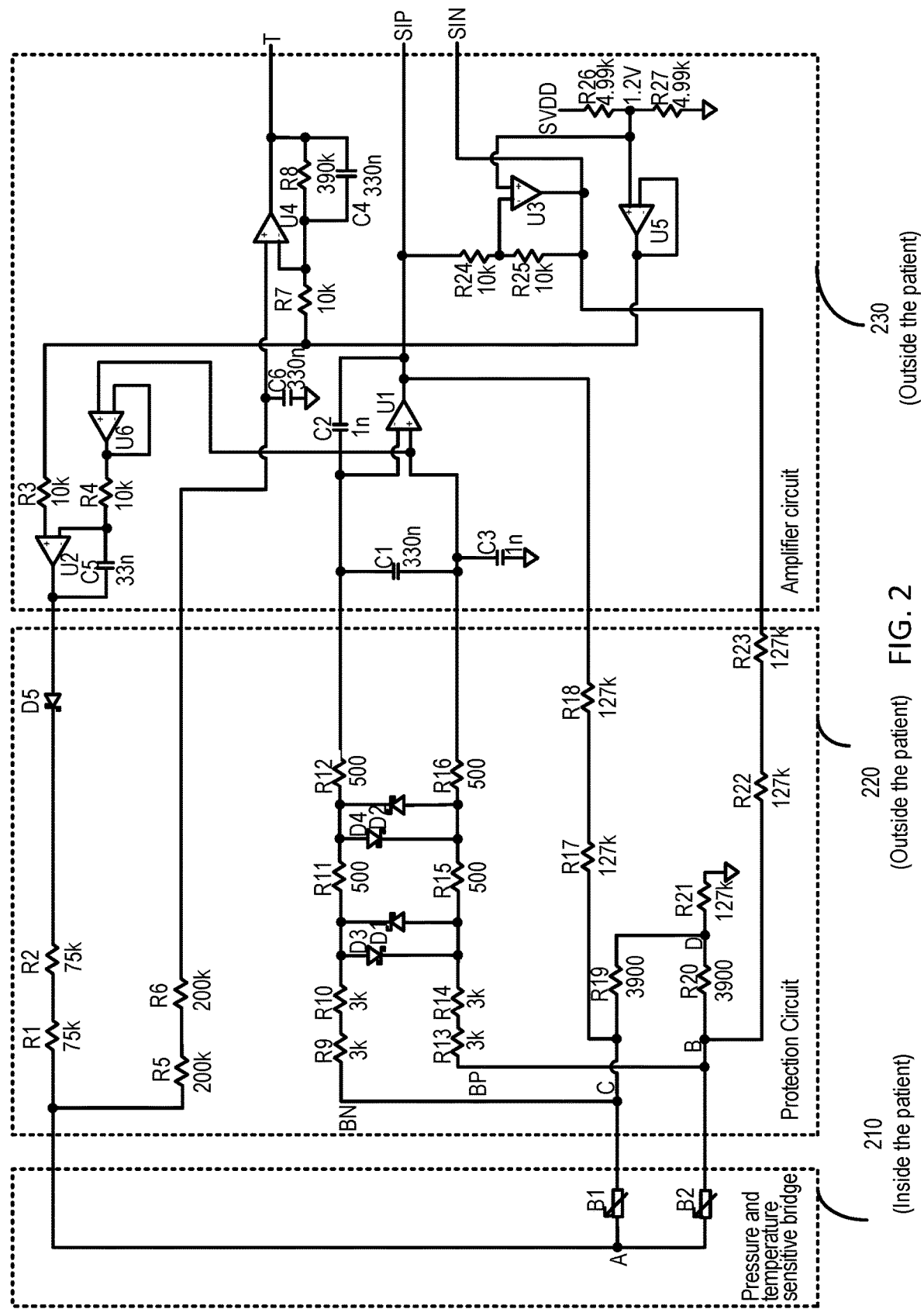
FIG. 2 is a schematic of a pressure sensing circuit according to an embodiment of the present invention.

The disclosed circuit is shown in FIG. 2. The circuit as drawn has three major blocks: Pressure and temperature sensitive bridge 210, patient protection circuitry 220, which comprises both current limiting elements (resistors) and voltage limiting elements (diodes), and amplification circuit 230. The amplification circuit 230 provides a nullification current to the bridge 210, effectively reducing the output voltage (voltage between nodes B and C) of the bridge 210 to zero. The differential output voltage (the voltage at SIP minus the voltage at SIN) used to generate the nullification current can then be used to provide an interpretable signal indicative of pressure.

Bridge Section 210:

Elements B1 and B2 are the pressure and temperature sensitive elements. Typically, these elements can be the active sensing elements for a pressure sensitive device that is attached to or inserted into a patient as part of a medical procedure.

The protection circuit 220 limits the currents that can pass between the three leads that connect the protection circuit 220 to the pressure and temperature sensitive bridge 210 and in doing so limits the currents that can be passed to the patient.

Amplifier Circuit 230:

Amplifiers U1 and U3 together form a differential output operational amplifier that is set up to null out the voltage on the bridge by supplying a balanced differential current to bridge nodes B and C through resistor pair R17 and R18 and pair R22 and R23. The differential output voltage at SIP and SIN used to supply the nulling current is an amplified version of the signal produced by the bridge. The gain of the system is determined by the resistance of the feedback resistors R17, R18, R22, and R23. Larger resistor values produce larger differential voltages between SIP and SIN. The voltage difference between SIP and SIN is substantially proportional to pressure. By nulling the voltage across the outputs of the bridge, the voltage across diodes D1 to D4 can be kept very close to zero. This prevents leakage currents through these diodes that can cause errors in the measured bridge signal. Amplifier U6 is a buffer amplifier that outputs the voltage on one of the bridge nodes (drawn as node B.) Amplifier U2 compares the output of amplifier U6 (the center voltage of one side of the bridge) with one half of a reference voltage (SVDD) and adjusts the bridge drive current into node A to keep these two voltages equal. This sets the common mode output voltage of the bridge circuit. Amplifier U4 amplifies the voltage difference between bridge nodes A and B. This voltage varies substantially linearly with the parallel resistance of the sensing elements B1 and B2, which in turn varies with the temperature of the sensing elements. The output of amplifier U4 is substantially proportional to temperature of the sensor. Amplifier U5 buffers one half of the reference voltage SVDD.

If reference voltage SVDD is also used as the reference voltage for an ADC measuring the difference between SIP and SIN, then the measurement of the difference in voltage between SIP and SIN is fully ratiometric with the voltage SVDD. This effectively removes much of the dependence on the voltage SVDD.

Protection Circuit 220:

Resistors R19 and R20 are passive (not pressure or temperature sensing) completing the bridge, and can generally be chosen to match the midrange-pressure condition of the sense resistors B1 and B2, which in turn can cause the voltages at nodes B and C to lie close to a voltage halfway between the voltages at nodes A and D. All of the resistors in the protection circuit limit patient auxiliary currents in normal or single fault conditions. Those with additional roles or considerations are mentioned in the following. Resistors R9 to R16 are on the input path to amplifier U1 and are a main source of noise (Johnson noise) in the pressure measurement. Resistors R5 and R6 are on the input path to amplifier U4 and are a primary source of noise (Johnson noise) in the temperature measurement. Resistors R17, R18, R22, and R23 are the feedback resistors used to provide nulling currents to the measurement nodes (B, C) of the bridge. Diode D5 allows current to flow in only one direction into the lead connected to node A of the bridge. This improves the performance of the protection circuitry. Diode pair D1 and D3 and diode pair D4 and D2 provide redundant limiting of the differential voltage at the input to amplifier U1. This serves to limit the current flowing between nodes B and C in a fault situation where B and C are directly connected to the patient (for example, if the patient connected sensor leads are severed and shorted to the patient). Limiting the voltage across these diodes permits resistors R9, R10, R13, and R14 to be smaller than would be permitted if this limiting was not in place. This serves the critical purpose of reducing the noise (Johnson noise) produced by these resistors. The capacitors control the frequency response of the circuit both to ensure stability of the feedback loops and to optimize the digitization of the output signal (for example, by reducing aliasing).

In summary, amplifiers U1, U2, and U3 drive nodes B and C to voltages near one-half the reference voltage SVDD, thereby greatly reducing the voltage across diodes D1 to D4.

In this example, bridge 210 can be at a distal end of a catheter or other device that is inserted into a patient (for example passing through a needle into an artery or vein within the patient). Protection circuit 220 and amplifier circuit 230 can be at a proximal end of the catheter, outside of the patient, and can be included with other circuitry and equipment. Leads for nodes A, B, and C can be routed through the catheter from protection circuit 220 to bridge 210. If node A is shorted to nodes B and C (for example, with the sensor severed in contact with the blood stream) through the patient, the resulting current could be approximately one-half the reference voltage of 1.2 volts divided by the series resistance of R21 and (R19 in parallel with R20), which would be less than 10 µA. Furthermore, protection circuit 220 is designed to limit the current through the patient to less than 50 µA when in addition to the sensor being severed and in contact with the patient any single protective component fails with either a shorted or an open impedance condition. More generally, the circuit described here can be used to limit currents to any desired level and with any desired input voltages (reference and amplifier supply voltages) by simply scaling the resistor values.

Amplifier U1 and amplifier U3 together can be configured as a differential in, differential out, differential amplifier with a common mode output voltage of SVDD/2 connected in a negative feedback arrangement with resistors R17 and R18 and R22 and R23 where the outputs of the differential amplifier adjust to essentially null out the differential input voltage. The outputs of the differential in/out composite amplifier are the output nodes SIP and SIN. The quiescent state where there is an absence of a pressure signal that could generate a differential signal between nodes B and C can be as follows. Amplifier U2 causes the voltage on node B to equal one half of the reference voltage SVDD. Without any pressure signal node C is symmetric to node B and node C may be at least approximately the same voltage as node B. Without any input difference between nodes B and C, the composite differential out amplifier U1/U3 brings both the SIP and the SIN nodes to SVDD/2.

As a pressure signal is applied, the resistances of sense elements B1 and B2 can diverge. For example, the resistance of B1 can increase and the resistance of B2 can decreased. Without feedback, this could cause the voltage on node B to increase and the voltage on node C to decrease. However, with feedback, the resulting differential output of the composite amplifier U1/U3 increases until the currents through resistors R17 and R18 as well as R22 and R23 are large enough to offset the pressure induced difference in the voltage of nodes B and C. That is, the feedback circuit adjusts the currents into or out of nodes B and C to ensure that the voltage across resistor R19 equals the voltage across resistor R20. Since these two resistors have nominally the same value the currents through these two resistors can be nominally equal. The resulting voltage between nodes SIP and SIN can be nominally proportional to the pressure induced change in the resistances of sensing elements B1 and B2. The ratio of the voltage produces to the pressure induced resistance change can be determined by the size of the feedback resistors (R17 and R18) and (R22 and R23). With large feedback resistors, the nulling currents through resistors R17 and R18, as well as R22 and R23, can be very small while generating a substantial output signal between output nodes SIP and SIN.

As the temperature of the bridge 210 changes, the common mode voltage at node A can change. Amplifier U4 can receive this changing common mode voltage and approximately one half the power supply voltage at its inputs, and generate an output signal that can be used to interpret the temperature of sense elements B1 and B2 in bridge 210.

In the example provided, the sense resistors B1 and B2 can have values of 3900 Ohms at the midrange-pressure condition, and the reference voltage SVDD can be 2.4V. In the example provided, the resistors can be chosen to limit the sum of the normal currents through sense resistors B1 and B2 to less than 10 µA and single fault currents to less than 50 µA when the supply voltages to the amplifiers are 3.0 V or less. Other (higher) values of the voltages (SVDD or the amplifier supply voltages) may be used if appropriate scaling of the remaining components (resistors) is carried out.

Also in this example, the diodes D1-D5 are shown as Schottky diodes, though other types of diodes can be used in these and other embodiments of the present invention. Bridge 210 Elements B1 and B2 can be formed on or near a membrane of a pressure sensor die. Protection circuit 220 and amplifier circuit 230 circuits can be formed on one or more integrated circuits, or they can be or include discrete components.

The above description of embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated. Thus, it will be appreciated that the invention is intended to cover all modifications and equivalents within the scope of the following claims.

What is claimed is:

1. A pre-amplifier circuit for a pressure sensor system, the pre-amplifier circuit comprising:
    a differential-output operational-amplifier having an inverting input, a noninverting input, and a differential output comprising a positive output and a negative output;
    a first node coupled to the positive output of the differential-output operational-amplifier, where the first node is configured to connect to a first side of a first external pressure-sensitive element;
    a second node coupled to the negative output of the differential-output operational-amplifier, where the second node is configured to connect to a first side of a second external pressure-sensitive element; and
    a protection circuit including a plurality of resistors coupled between the first node and the inverting input of the differential-output operational-amplifier, and between the second node and the noninverting input of the differential-output operational-amplifier.

2. The pre-amplifier circuit of claim 1 further comprising:
    a third node, where the third node is configured to connect to a second side of the first external pressure-sensitive element and a second side of the second external pressure-sensitive element; and
    a first amplifier coupled to the third node to set a common-mode voltage at the first node and the second node.

3. The pre-amplifier circuit of claim 2 further comprising:
    a second amplifier having an input coupled to the third terminal and an output; and
    a fourth node coupled to the output of the second amplifier.

4. The pre-amplifier circuit of claim 3 further comprising:
    a first resistor coupled to the first node; and
    a second resistor coupled to the second node.

5. The pre-amplifier circuit of claim 4 wherein the first external pressure-sensitive element, the second external pressure-sensitive element, the first resistor, and the second resistor form a Wheatstone bridge.

6. The pre-amplifier circuit of claim 5 wherein the first node is coupled to the positive output of the differential-output operational-amplifier through a third resistor and the second node is coupled to the negative output of the differential-output operational-amplifier through a fourth resistor.

7. The pre-amplifier circuit of claim 6 wherein the protection circuit comprises:
    a first series of resistors coupled between the first node and the inverting input of the differential-output operational-amplifier; and
    a second series of resistors coupled between the second node and the noninverting input of the differential-output operational-amplifier.

8. The pre-amplifier circuit of claim 7 further comprising a plurality of diodes coupled between the first series of resistors and the second series of resistors.

9. The pre-amplifier circuit of claim 8 wherein the plurality of diodes are arranged in a back-to-back configuration.

10. The pre-amplifier circuit of claim 9 wherein the first external pressure-sensitive element and the second external pressure-sensitive element are resistors.

11. A pressure-sensing system comprising:
a Wheatstone bridge having an input, a first output, and a second output, the Wheatstone bridge comprising:
a first pressure-sensitive element coupled between the input and the first output;
a second pressure-sensitive element coupled between the input and the second output;
a first resistor coupled between the first output and ground; and
a second resistor coupled between the second output and ground;
a differential-output operational-amplifier to provide a first current to the first output and a second current to the second output such that a resulting voltage between the first output and the second output is minimized; and
a protection circuit including a plurality of resistors coupled between the first output and the differential-output operational amplifier, and between the second node and the differential-output operational amplifier.

12. The pressure-sensing system of claim 11 further comprising a first amplifier to provide an input current to the input such that a resulting voltage between the input and the second output is minimized.

13. The pressure-sensing system of claim 12 wherein the protection circuit increases an impedance between the Wheatstone bridge and inputs of the differential-output operational-amplifier.

14. The pressure-sensing system of claim 13 further comprising a second amplifier to provide a temperature related signal based on a voltage at the input of the Wheatstone bridge.

15. The pressure-sensing system of claim 11 wherein the first pressure-sensitive element and the second pressure-sensitive element are on a first integrated circuit and the first resistor, second resistor, and differential-output operational-amplifier are on a second integrated circuit.

16. The pressure-sensing system of claim 11 wherein the first pressure-sensitive element and the second pressure-sensitive element are resistors.

17. A pre-amplifier circuit for a pressure sensor system, the pre-amplifier circuit comprising:
a differential-output operational-amplifier;
a protection circuit comprising:
a first series of resistors coupled between a first node and an inverting input of the differential-output operational-amplifier; and
a second series of resistors coupled between a second node and a noninverting input of the differential-output operational-amplifier;
a third series of resistors coupled between a positive output of the differential-output operational-amplifier and the first node;
a fourth series of resistors coupled between a negative output of the differential-output operational-amplifier and the second node;
a first resistor coupled between the first node and ground; and
a second resistor coupled between the second node and ground.

18. The pre-amplifier circuit of claim 17 further comprising a plurality of back-to-back diodes coupled between the first series of resistors and the second series of resistors.

19. The pre-amplifier circuit of claim 18 wherein the differential-output operational-amplifier is configured to reduce a voltage between the first node and the second node during operation.

20. The pre-amplifier circuit of claim 19 wherein the positive output of the differential-output operational-amplifier is coupled to a third node and the negative output of the differential-output operational-amplifier is coupled to a fourth node.

* * * * *